United States Patent [19]
Eisele et al.

[11] Patent Number: 5,939,389
[45] Date of Patent: Aug. 17, 1999

[54] USE OF C1-INACTIVATION FOR THERAPY OF CERTAIN DISEASES

[75] Inventors: Bernd Eisele, Gossfelden; Ulrich Delvos, Giessen; Andreas Jessel, Marburg, all of Germany

[73] Assignee: Behringwerke Aktiengesellschaft, D-35001 Marburg, Germany

[21] Appl. No.: 08/854,365

[22] Filed: May 12, 1997

Related U.S. Application Data

[63] Continuation of application No. 08/677,789, Jul. 10, 1996, abandoned, which is a continuation of application No. 08/468,331, Jun. 6, 1995, abandoned, which is a continuation of application No. 08/369,338, Jan. 6, 1995, abandoned, which is a continuation of application No. 08/109,492, Aug. 20, 1993, abandoned.

[30] Foreign Application Priority Data

Aug. 24, 1992 [DE] Germany ............... 42 27 762

[51] Int. Cl.$^6$ ............ A61K 38/43; A61K 38/16
[52] U.S. Cl. ............... 514/12; 514/2; 530/830; 424/94.1
[58] Field of Search ............... 530/830; 514/2, 514/12; 424/94.1

[56] References Cited

U.S. PATENT DOCUMENTS

| | | | |
|---|---|---|---|
| 4,915,945 | 4/1990 | Pelzer et al. | 421/101 |
| 5,030,578 | 7/1991 | Pilatte et al. | 436/86 |
| 5,271,931 | 12/1993 | Lotz et al. | 424/85.5 |

FOREIGN PATENT DOCUMENTS

| | | |
|---|---|---|
| 2104636 | 2/1994 | Canada . |
| 586 909 | 3/1994 | European Pat. Off. . |
| 42 27 735 | 3/1994 | Germany . |
| 42 27 762 | 3/1994 | Germany . |
| 90 02570 | 3/1990 | WIPO . |
| 92 06706 | 4/1992 | WIPO . |
| 92/22320 | 12/1992 | WIPO . |

OTHER PUBLICATIONS

H.F. Welter et al. "Versuche zur Therapie der Schoklunge mittels Superoxiddismutase (SOD) und C1–Inaktivator (C1–INA)," *Langenbecks Archiv fur Chirugie, Chirurgisches Forum '85*, 1985, pp. 63–67.

W. Nurnberger et al., "C1–inhibitor concentrate for sepsis–related capillary leak syndrome," *Lancet*, 1992, vol. 339, p. 990.

van der Starre et al. (1980) *J. Thorac. Cardiovasc. Surg.* 79: 738–40.

Farber et al. (1992) *Lancet* 339: 119.

Bosner et al. (1991) *Ann. Thorac. Surg.* 52: 541–3.

Nürnberger et al. (1993) *Ann. Hematol.* 67: 17–21.

*Primary Examiner*—Lila Feisee
*Assistant Examiner*—Claire M. Kaufman
*Attorney, Agent, or Firm*—Finnegan, Henderson, Farabow, Garrett & Dunner, L.L.P.

[57] ABSTRACT

The use of C1-inactivator for the production of a pharmaceutical for the prophylaxis and treatment of capillary leak syndrome (generalized extravasation) and circulator shock (refractory hypotension) in severe burns or scalds, in polytrauma, in operations under conditions of extracorporeal circulation, in the use of cytokines, endogenous mediators, and mediator hybrids and growth factors produced by genetic engineering, or capillary leak syndrome and venoocclusive disease of the liver in therapeutically or prophylactically indicated bone marrow transplantation is described.

10 Claims, No Drawings

USE OF C1-INACTIVATION FOR THERAPY OF CERTAIN DISEASES

This application is a continuation of application Ser. No. 08/677,789 filed Jul. 10, 1996, now abandoned, which is a continuation of application Ser. No. 08/468,331, filed Jun. 6, 1995, now abandoned, which is a continuation of application Ser. No. 08/369,338, filed Jan. 6, 1995, now abandoned, which is a continuation of application Ser. No. 08/109,492, filed Aug. 20, 1993, now abandoned.

The invention relates to the use of C1-inactivator for the production of a pharmaceutical for the prophylaxis and treatment of capillary leak syndrome (generalized extravasation) and circulatory shock (refractory hypotension) in severe burns or scalds, in polytrauma, in operations under conditions of extracorporeal circulation, in the use of cytokines, endogenous mediators, and mediator hybrids and growth factors produced by genetic engineering or capillary leak syndrome and veno-occlusive disease of the liver in therapeutically or prophylactically indicated bone marrow transplantation.

The kallikrein system consists of a number of proteases and intermediate products which, after initial activation, lead successively to the formation of vasoactive kinins (for example, bradykinin). The decisive quantity is the amount of proteolytically active kallikrein.

The activation of the kallikrein system can take place as a result of direct action of the damaging mechanisms, but also indirectly by the generation of C-reactive protein in the course of an acute phase reaction, possibly with the interposition of further protease systems.

However, independently of the underlying trigger mechanisms, the further course of the pathophysiological events is dependent on the capability of the organism to regulate the formation of kallikrein and to control the proteolytic activity of the generated kallikrein to an adequate extent by means of sufficient degradation or inhibition.

The most important physiological regulator of the kallikrein system under in vivo conditions is C1-inactivator. It displays its action on the central site of the system by interaction with the activated protease kallikrein and inhibition thereof.

The activation of the kallikrein system is observed in the course of a number of diseases and also in the course of therapeutic and/or prophylactic iatrogenic interventions. These activation processes are generally associated with a consumption of the factors involved, in particular of the inhibitor.

Although, as a result of the acute phase reaction, an excess production of C1-inactivator is to be observed, its inhibitory capacity is not sufficient to control the activation of the kallikrein system.

The etiopathogenesis of the occurrence of shock and of generalized edema in patients with severe burns is as follows: the heat trauma leads to an acute phase reaction and to the (indirect and/or direct) activation of the kallikrein system. If the inhibitor potential of the body is used up, unhindered activation and uncontrolled release of toxic intermediate products (for example kallikrein) takes place and also of likewise potentially harmful end products (kinins, especially (esp. bradykinin). This is documented, inter alia, in the knowledge that in patients with heat trauma the substrate "prekallikrein" (as a measure of the formation of kallikrein and bradykinin) is decreased as a function of the severity of the heat-injury. The substances mentioned have the potential to affect the vascular endothelium directly. However, as a result of activation of secondary mechanisms (for example, NO [nitric oxide], cGMP [cyclic guanosine monophosphate]), they can lead to indirect damage either in the endothelial cell wall or in the endothelium itself. The pathomorphological result of the harmful effects on the endothelium are an extravasation from the vascular system and/or the decreased response of the vascular musculature to vasoconstrictor impulses. Clinical symptoms in the patients are generalized edema and refractory hypotension (circulatory shock).

Pathogenically, the substances mentioned have the potential to affect the vascular endothelium directly. However, as a result of activation of secondary mechanisms (for example, NO, cGMP), they can either lead to indirect damage in the endothelial cell wall or in the endothelium itself. The pathomorphological result of the harmful effects on the endothelium are an extravasation from the vascular system and/or the decreased response of the vascular musculature to vasoconstrictor impulses. Clinical symptoms in the patients are generalized edema and refractory hypotension (circulatory shock).

The etiopathogenesis of the occurrence of shock and of generalized edema in patients with acute pancreatitis is as follows: either the inflammatory process itself, via the release of aggressive proteases (for example, trypsin), or the underlying mechanism inducing the inflammatory process leads to an acute phase reaction and to the (indirect and/or direct) activation of the kallikrein system. If the inhibitor potential of the organism is used up, unhindered activation of this system takes place with uncontrolled release of toxic intermediate products (for example, kallikrein) and also of likewise potentially harmful end products (kinins, esp. bradykinin).

In patients with acute pancreatitis, it is seen that the extent of the activation of the kallikrein system correlates with the severity of the disease. A dysregulated increased activation in patients was coincidental with the occurrence of circulatory shock.

Pathogenically, the substances mentioned have the potential to affect the vascular endothelium directly. However, as a result of activation of secondary mechanisms (for example, NO, cGMP), they can either lead to indirect damage in the endothelial cell wall or in the endothelium itself. The pathomorphological result of the harmful effects on the endothelium are an extravasation from the vascular system and/or the decreased response of the vascular musculature to vasoconstrictor impulses. Clinical symptoms in the patients are generalized edema and refractory hypotension (circulatory shock).

The etiopathogenesis of the occurrence of shock in patients with polytrauma is as follows: the trauma itself or the resulting damage in the body (unstable fractures, necrotic tissue) lead to an acute phase reaction and to the (indirect and/or direct) activation of the kallikrein system. If the inhibitor potential of the organism is used up, unhindered activation of this system takes place with uncontrolled release of toxic intermediate products (for example, kallikrein) and also of likewise potentially harmful end products (kinins, esp. bradykinin). These substances have the potential to affect the vascular endothelium directly. However, as a result of activation of secondary mechanisms (for example, NO, cGMP), they can lead to indirect damage either in the endothelial cell wall or in the endothelium itself. In diagnostic investigations in patients with polytrauma, the substrate "prekallikrein" (as a measure of the formation of kallikrein and bradykinin) is found to be decreased. The extent of the decrease correlates with the severity of the injury. The pathomorphologic result of the harmful effects on the endothelium are an extravasation from the vascular system, but especially the decreased response of the vascular musculature to vasoconstrictor impulses. The predominant clinical symptom in the patient is refractory hypotension (circulatory shock).

The etiopathogenesis of the occurrence of shock and of generalized edema in patients in the state after therapeutically or prophylactically indicated bone marrow transplantation is as follows: ablative pretreatment (chemotherapy and/or radiotherapy) by itself or else in cooperation with the subsequent bone marrow transplantation leads to an acute phase reaction and to the (indirect and/or direct) activation of the kallikrein system. If the inhibitor potential of the organism is used up, unhindered activation of this system takes place with uncontrolled release of toxic intermediate products (for example, kallikrein) and also of likewise potentially harmful end products (kinins, esp. bradykinin). These substances have the potential to affect the vascular endothelium directly. However, as a result of activation of secondary mechanisms (for example, NO, CGMP) they can also lead to indirect damage in the endothelial cell wall or in the endothelium itself. The pathomorphological result of the harmful effects on the endothelium are an extravasation from the vascular system and/or the decreased response of the vascular musculature to vasoconstrictor impulses. Clinical symptoms in the patient are so-called "veno-occlusive disease", generalized edema and refractory hypotension (circulatory shock) and/or a progressive dysfunction of one or more organ systems.

From diagnostic studies in humans, it is known that the occurrence of life-threatening complications (generalized edema and/or circulatory shock) is associated with the symptom of dysregulated activation of the kallikrein system. Complication-free intervals are accompanied by a normalization of the laboratory parameters.

The etiopathogenesis of the occurrence of shock and of generalized edema in patients who undergo operations under the conditions of an extracorporeal circulation (bubble or membrane oxygenators) is as follows: the contact of the blood with the foreign surfaces, or its interaction with the oxygen bubbles, of the oxygenator lead to an acute phase reaction and to the (indirect and/or direct) activation of the kallikrein system. If the inhibitor potential of the organism is used up, unhindered activation of this system takes place with uncontrolled release of toxic intermediate products (for example, kallikrein) and also of likewise potentially harmful end products (kinins, esp. bradykinin). These substances have the potential to affect the vascular endothelium directly. However, as a result of activation of secondary mechanisms (for example, NO, cGMP), they can also lead to indirect damage either in the endothelial cell wall or in the endothelium itself. The pathomorphological result of the harmful effects on the endothelium are an extravasation from the vascular system and/or the decreased response of the vascular musculature to vasoconstrictory impulses. Clinical peri- and post-operative symptoms in the patient are generalized edema and/or refractory hypotension (circulatory shock) and/or a reduction in the cardiac output.

The etiopathogenesis of the occurrence of shock and of generalized edema in patients under administration of cytokines, endogenous mediators, mediator hybrids, and growth factors produced by genetic engineering in the course of the therapeutic use of these substances individually in combination with one another or in combination with other therapeutic or prophylactic measures is as follows: the administration of these above-mentioned substances, individually, in combination with one another or in combination with other therapeutic or prophylactic measures leads to an acute phase reaction and to the (indirect and/or direct) activation of the kallikrein system. If the inhibitor potential of the organism is used up, unhindered activation of this system takes place with uncontrolled release of toxic intermediate products (for example, kallikrein) and also of likewise potentially harmful end products (kinins, esp. bradykinin).

The pathogenetic potential of these substances is that they are directly able to affect the vascular endothelium. However, as a result of activation of secondary mechanisms (for example, NO, cGMP) they can also lead to indirect damage either in the endothelial cell wall or in the endothelium itself. In addition, however, some of the above-mentioned cytokines, endogenous mediators and growth factors (for example, interleukin-1β, tumor necrosis factor, and interferons) can also have a damaging effect directly on the endothelium. Others, however, also have an indirect effect in that they induce increased production or activation of the directly damaging cytokines. In some of the cytokines, endogenous mediators and growth factors, it has still not been possible to elucidate the exact pathological mechanism of the endothelial damage. The pathomorphological result of the damaging effects on the endothelium are an extravasation from the vascular system and/or the decreased response of the vascular musculature to vasoconstrictor impulses. Clinical symptoms in the patient are generalized edema and refractory hypotension (circulatory shock).

Accordingly, severe burns, polytrauma, therapeutic or prophylactically indicated bone marrow transplantations, operations under conditions of extracorporeal circulation and also the therapeutic or prophylactic use of cytokines, endogenous mediators, and mediator hybrids and growth factors produced by genetic engineering have, as an accompanying symptom, generalized edema and refractory hypotension (circulatory shock) in common. The symptoms mentioned are often seen after activation of the kallikrein system.

We have now found that the administration of C1-inactivator has a positive effect in the treatment of generalized edema, refractory hypotension (circulatory shock), progressive dysfunction of organ systems and reduced cardiac output (in patients under extracorporeal circulation).

The invention accordingly relates to the use of C1-inactivator for the production of a pharmaceutical for the prophylaxis and treatment of capillary leak syndrome (generalized extravasation) and circulator shock (refractory hypotension) in severe burns or scalds, in polytrauma, in operations under conditions of extracorporeal circulation, in the use of cytokines, endogenous mediators, and mediator hybrids and growth factors produced by genetic engineering, or capillary leak syndrome and veno-occlusive disease of the liver in therapeutically or prophylactically indicated bone marrow transplantation.

C1-inactivator can be prepared from blood plasma in a manner known to the person skilled in the art, and preferably as a purified product.

C1-inactivator is known as a pyrogen free lyophilisate, which is dissolved before administration and preferably injected intravenously. One unit of the C1-inactivator concentrate corresponds to the activity of 1 ml of pooled human citrate plasma (1 unit [1 U] thus corresponds to 6 Levy & Lepow units).

C1-inactivator expressed by genetic engineering and purified can also be employed for the production of the pharmaceutical.

The pharmaceutical can be prepared for intravenous (bolus or infusion), intramuscular or subcutaneous administration.

The pharmaceutical contains 1–5,000 U/kg of bodyweight (BW)/day, preferably 5–1,000 U/kg BW/day of C1-inactivator.

For adults, a solid pharmaceutical having a dose of 1–300,000 U/day, preferably 50–60,000 U/day of C1-inactivator, can also be prepared.

C1-inactivator can be used separately or as a combination with other pharmaceutical substances. Particularly in combination with pharmaceutical auxiliaries, the production of an oral or rectal form is also possible.

EXAMPLE OF CLINICAL USES OF THE PHARMACEUTICAL ACCORDING TO THE INVENTION

In patients with generalized edema and refractory hypotension (circulatory shock) in the course of heat injuries (burning, scalding), the high-dose intravenous use of C1-inactivator concentrate led to breaking of refractory hypotension and also to improvement of generalized edema. The therapeutic administration scheme used was as follows:

initially 5,000 U of C1-inactivator i.v., after 12 hours 2,500 U of C1-inactivator i.v., after a further 12 hours 1,500 U of C1-inactivator l.v., after a further 12 hours 1,000 U of C1-inactivator l.v.

In patients with polytrauma, the use of C1-inactivator concentrate led to the correction of the desperate circulatory situation. The treatment schemes used differed, but varied in order of magnitude from 1,000 to 6,000 U of C1-inactivator concentrate i.v. and were, as a rule, administered repetitively at 12 hour intervals.

In patients with therapeutically or prophylactically indicated bone marrow transplantation, C1-inactivator concentrate was employed i.v. in two patients. The dose scheme was:

initially 60 U/kg of BW after 12 hours: 30 U/kg of BW after 12 hours: 30 U/kg of BW after 12 hours: 15 U/kg of BW after 12 hours: 15 U/kg of BW after 12 hours: 15 U/kg of BW after 12 hours: 15 U/kg of BW In these patients, successful treatment of generalized edema, the beginnings of "veno-occlusive disease" and also (in one case) the beginnings of renal failure was possible.

In patients who have been subjected to an operation under conditions of extracorporeal circulation, C1-inactivator concentrate was administered i.v. in 56 patients altogether. In 55 patients, this was carried out in the course of a clinical trial in the indication "bypass operation", in one patient, a newborn child, this was carried out in the course of a therapeutic "off label" use during a so-called transposition operation of the aorta and pulmonary artery. The results were as follows:

In the adult patients who received C1-inactivator concentrate in the course of a bypass operation, it was possible to distinctly improve this cardiac output in the peri- and post-operative course in those who preoperatively suffered from a reduced cardiac output. In the newborn child, a generalized edema occurred in the post-operative course. It was possible to control this successfully with C1-inactivator concentrate and the edema resolved.

We claim:

1. A pharmaceutical composition, comprising an amount of C1-inactivator effective for the treatment of
   (a) capillary leak syndrome and circulatory shock due to (i) severe burns or scalds, or (ii) the use of cytokines or growth factors, produced by genetic engineering; or
   (b) capillary leak syndrome or veno-occlusive disease of the liver due to therapeutically or prophylactically indicated bone marrow transplantation;
   and a pharmaceutical carrier or diluent.

2. The composition as claimed in claim 1, wherein the pharmaceutical carrier or diluent is suitable for intravenous, intramuscular or subcutaneous administration.

3. The composition as claimed in claim 1, wherein the pharmaceutical carrier or diluent is suitable for oral or rectal administration.

4. A method for the treatment of
   (a) capillary leak syndrome and circulatory shock due to (i) severe burns or scalds, or (ii) the use of cytokines or growth factors, produced by genetic engineering; or
   (b) capillary leak syndrome or veno-occlusive disease of the liver due to therapeutically or prophylactically indicated bone marrow transplantation,
   said method comprising administering to a host an effective amount of C1-inactivator.

5. The method as claimed in claim 4, wherein said amount is from 1 to 5,000 U/kg BW/day of C1-activator.

6. The method as claimed in claim 4, wherein said amount is from 1 to 300,000 U/BW/day of C1-inactivator.

7. The method as claimed in claim 4, wherein said C-1 inactivator is administered intravenously, intramuscularly or subcutaneously.

8. The method as claimed in claim 4, wherein said C-1 inactivator is administered orally or rectally.

9. The method as claimed in claim 5, wherein said amount is from 5 to 1,000 U/kg BW/day of C1-inactivator.

10. The composition as claimed in claim 6, wherein said amount is from 50 to 60,000 U/BW/day of C-1 inactivator.

* * * * *

UNITED STATES PATENT AND TRADEMARK OFFICE
CERTIFICATE OF CORRECTION

PATENT NO. : 5,939,389
DATED : August 17, 1999
INVENTOR(S) : Bernd Eisele et al.

It is certified that error appears in the above-identified patent and that said Letters Patent is hereby corrected as shown below:

Column 6,
Line 40, "C1-activator" should read -- C1-inactivator --.

Signed and Sealed this

Twenty-fifth Day of February, 2003

JAMES E. ROGAN
*Director of the United States Patent and Trademark Office*